US00PP30019P3

(12) United States Plant Patent
Čerenak et al.

(10) Patent No.: US PP30,019 P3
(45) Date of Patent: Dec. 25, 2018

(54) HOP PLANT NAMED '74/134'

(50) Latin Name: ***Humulus lupulus* L.**
Varietal Denomination: 74/134

(71) Applicant: INŠTITUT ZA HMELJARSTVO IN PIVOVARSTVO SLOVENIJE, Žalec (SI)

(72) Inventors: Andreja Čerenak, Žalec (SI); Monika Oset Luskar, Žalec (SI); Sebastjan Radišek, Žalec (SI); Iztok Jože Košir, Žalec (SI)

(73) Assignee: INSTITUT ZA HMELJARSTVO IN PIVOVARSTVO SLOVENIJE (SI)

( * ) Notice: Subject to any disclaimer, the term of this patent is extended or adjusted under 35 U.S.C. 154(b) by 0 days.

(21) Appl. No.: 15/731,224

(22) Filed: May 5, 2017

(65) Prior Publication Data

US 2018/0324994 P1 Nov. 8, 2018

(51) Int. Cl.
*A01H 5/00* (2018.01)
*A01H 6/00* (2018.01)
*A01H 5/02* (2018.01)

(52) U.S. Cl.
USPC ..... Plt./236
CPC ..... *A01H 6/00* (2018.05); *A01H 5/02* (2013.01)

(58) Field of Classification Search
USPC ..... Plt./236
See application file for complete search history.

*Primary Examiner* — Susan McCormick Ewoldt
(74) *Attorney, Agent, or Firm* — Bryant J. Keller; Kirton McConkie

(57) ABSTRACT

A new and distinct aroma variety of hop, *Humulus lupulus* L., named '74/134' is characterized by high yield and intense, distinguishable fruity (passion fruit, mango, melon, lemon grass, and menthol) aroma.

3 Drawing Sheets

Latin name of the genus and species of the plant claimed: *Humulus lupulus* L.

Variety denomination: '74/134' also known as a 'STYRIAN WOLF™' hop plant.

BACKGROUND OF THE INVENTION

Hop (*Humulus lupulus* L.) is a perennial herbaceous climbing plant from the Cannabaceae family. It is native to Europe, western Asia, and North America. Only female plants are grown in hop fields, while male ones are not desired, to prevent the pollination of the female plants. Male hop plants have no commercial value other than for use in breeding programs to create new varieties. The life expectancy of hop plant is from ten to twenty years and depends mainly on the growing conditions, variety, and agricultural practices. The hop plant includes above-ground and below-ground vegetative parts. Normally, the above-ground parts of the plant die back to ground level every winter, but below-ground parts (or rootstock) are perennial. The commercial value of hops lies in the lupuline glands that contain resins (α-acid, β-acid) which give beer its bitterness and essential oils which contribute to beer flavor. New hop varieties are evaluated in terms of their growing characteristics, hop cone yields, disease resistance, hop resins, and essential oil components.

The flowers (cones) of the female hop plant, *Humulus lupulus* L., are used in the making of beverages, especially beer, as a flavoring and processing component. Hops contribute towards the bitterness and aroma in beer as well as foam quality, flavor, and taste stability. Various hop varieties have various special uses in the beer brewing industry. Aroma hops are used to impart flavors by virtue of the distinct profiles of their essential oils and terpene alcohols, among other compounds, as well as to supply bitter flavors based on specific contents of bitter acids, namely, terpenophenolics, mostly humulones.

BRIEF SUMMARY OF THE INVENTION

The present invention relates to a novel asexually reproduced hop variety invented in a planned and systematically executed breeding program. In this regard, the inventive hop is a product of breeding program carried out by the inventors in Slovenia. '74/134' was one of the several seedlings resulting from the cross between '272/138' ('200/22' x '2/1'; not patented) and Slovenian autochthonous male '2/137' (not patented). The inventive hop has been observed to retain intense, distinguishable fruity (passion fruit, mango, melon, lemon grass, menthol) aroma. It is a high-yielded variety with nice, tight cones bearing high alpha-acid content and having an intense aroma. It is clearly distinguishable from parental breeding lines, and other known varieties. Indeed, with respect to the parent male plant '2/137', while an upper surface of blades of such plant have a relatively bright color (e.g., RHS 137C), blades of '74/134' typically have a darker upper surface color (e.g., RHS 137B, as set forth below). Moreover, while '2/137' typically flowers between June 25$^{th}$ and July 5$^{th}$, '74/134' typically flowers between July 1$^{st}$ and August 10$^{th}$, as set forth below. Additionally, while '2/137' is a plant having a cylindrical to conical shape appearance, '74/134' is a plant having a cylindrical to club-shaped appearance, as set forth below. Also, while '2/137' has a medium plant volume of head, '74/134' typically has a high plant volume of head. With reference to the distinguishing features between the mother plant '272/138' and '74/134', '272/138' typically has blades that are darker (e.g., RHS 139A) than those of '74/134'

(which are typically RHS 137B, as mentioned above). Additionally, while '272/138' has a medium bract ratio with/length, '74/134' typically has a large ratio, as set forth below. Moreover, while '272/138' often has an average of 50 cones for a side shoot on an upper third of the plant, '74/134' often has an average of about 70 cones per node for a side shoot on an upper third of the plant, as set forth below. Furthermore, while bracts of '272/138' are slightly open, bracts of '74/134' are often closed, as mentioned below. In addition, while cones of '272/138' are often dark green, cones of '74/134' often have a medium green color, as set forth below. In addition to the foregoing, while '272/138' produces hop cones having a relatively weak hoppy aroma, '74/134' produces hop cones having a relatively intense and fruity aroma, as discussed herein. Moreover, while '272/138' has a yield of between about 1600 and 1750 pounds per acre, '74/134' typically has a higher average yield of between about 1800 and about 2200 pounds per acre. Thus, '74/134' is readily distinguishable from its breeding lines.

Moreover, '74/134' is readily distinguishable from other known hop varieties. For instance, '74/134' is distinguishable from the Slovenian hop variety known as 'Aurora', since on the main shoot of '74/134' plants anthocyanin coloration is absent, while in 'Aurora' plants anthocyanin coloration is often present though relatively weak. Moreover, while '74/134' typically flowers between July 1$^{st}$ and August 10$^{th}$, 'Aurora' typically flowers from June 25$^{th}$ till July 20$^{th}$. Additionally, 'Aurora's' time for picking mature cones is typically from August 25$^{th}$ till September 5$^{th}$, while '74/134' is typically a late variety having a harvest time from September 1$^{st}$ till September 10$^{th}$. Also, while 'Aurora' is a plant having a cylindrical shape appearance and plants (such as 'Nugget') are typically club-shaped, '74/134' plants are typically cylindrical to club-shaped. Additionally, while '74/134' has high plant volume of head, 'Aurora' has medium and 'Nugget' typically as a very high plant volume of head. In comparison to 'Aurora', '74/134' often has longer side shoots from an upper third of plant. In contrast, '74/134' often has a medium density of foliage on side shoots from a middle third of '74/134' plants, while 'Aurora' typically has sparse foliage in such locations and (on the other hand) 'Nugget' often expresses dense foliage on such part of the plant.

Furthermore, while 'Aurora' often has an average of 50 cones on a side shoot of an upper third of the plant, '74/134' has often an average of about 70 cones per node for a side shoot on an upper third of the plant. Regarding the degree of opening of bracts, '74/134' often has closed cones while in the case of the varieties of 'Aurora' and 'Nugget', the cones are often slightly opened. Additionally, 'Nugget' has larger bracteoles than those of '74/134'. Moreover, the ratio between width and length of bracts is typically lower in 'Aurora' cones than in '74/134' cones. Similarly, the length of an apex of bracteoles of 'Aurora' is often about 2 mm longer than the length of '74/134' bracts. Thus, '74/134' is readily distinguishable from other known hop varieties, such as the Slovenian variety 'Aurora' and the American variety 'Nugget'.

The hop with breeder's reference '74/134' (also known as a 'STYRIAN WOLF™', hop plant) is a product of a breeding program carried out by the inventors. '74/134' was one of the several seedlings resulting from the cross between '272/138' (200/22 x 2/1; not patented) and Slovenian autochthonous male '2/137' (not patented). Seedlings were then raised from the cross-pollination and planted on the field in late autumn. The plant was then observed as a single plant and later it was multiplied for the 5-plant block trial, where it was observed. It was then observed on three locations in Slovenia, in Žalec and in Gomilsko, both in Savinja Valley, and in Turiska vas, region of Carinthia, Slovenia. Before propagation virus and viroid mother plants were selected, the plants were maintained as a rootstock in a greenhouse. '74/134' has been observed to retain intense, distinguishable fruity (passion fruit, mango, melon, lemon grass, menthol) aroma. It is clearly distinguishable from parental breeding lines, and other known varieties. It is a high-yielded variety with nice, tight cones bearing high alpha-acid content and intense aroma.

BRIEF DESCRIPTION OF THE DRAWINGS

The accompanying photographs illustrate the leaves, cones, and growth habit of the new hops variety.

DETAILED BOTANICAL DESCRIPTION

Figure 1:
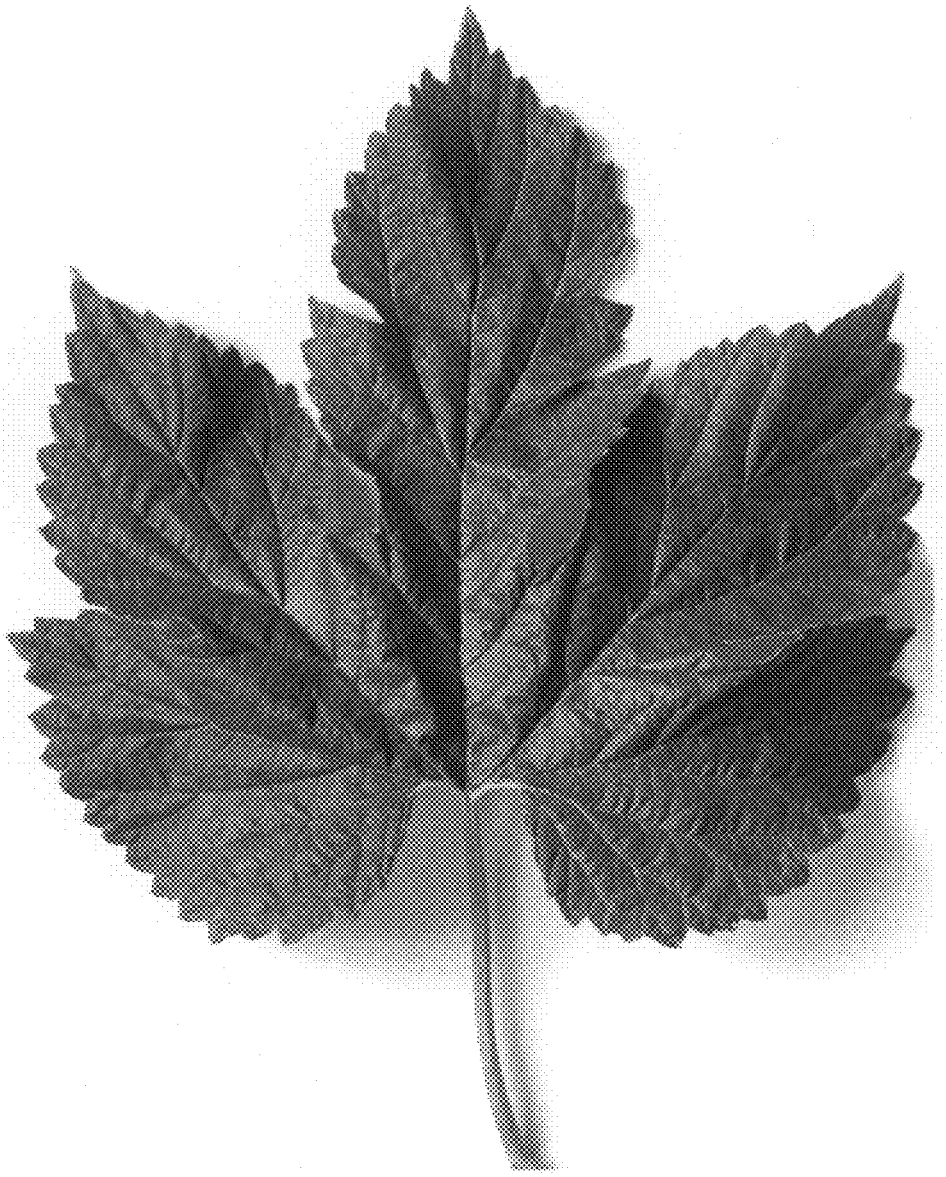
FIG. 1 illustrates a close up of a single leaf.
Figure 2:
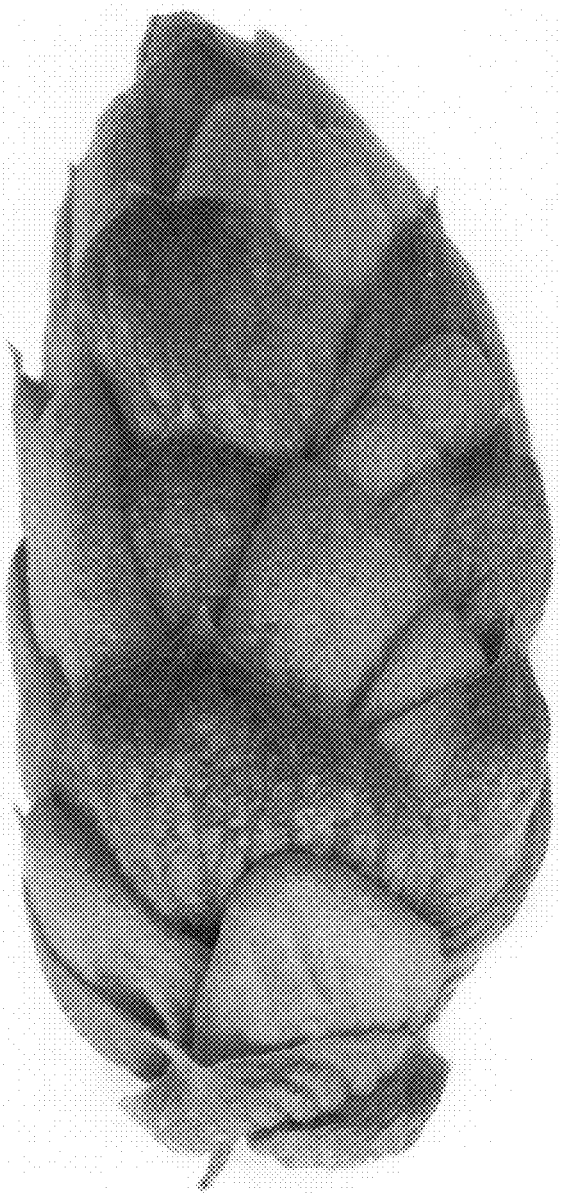
FIG. 2 illustrates a close up of a single cone.
Figure 3:
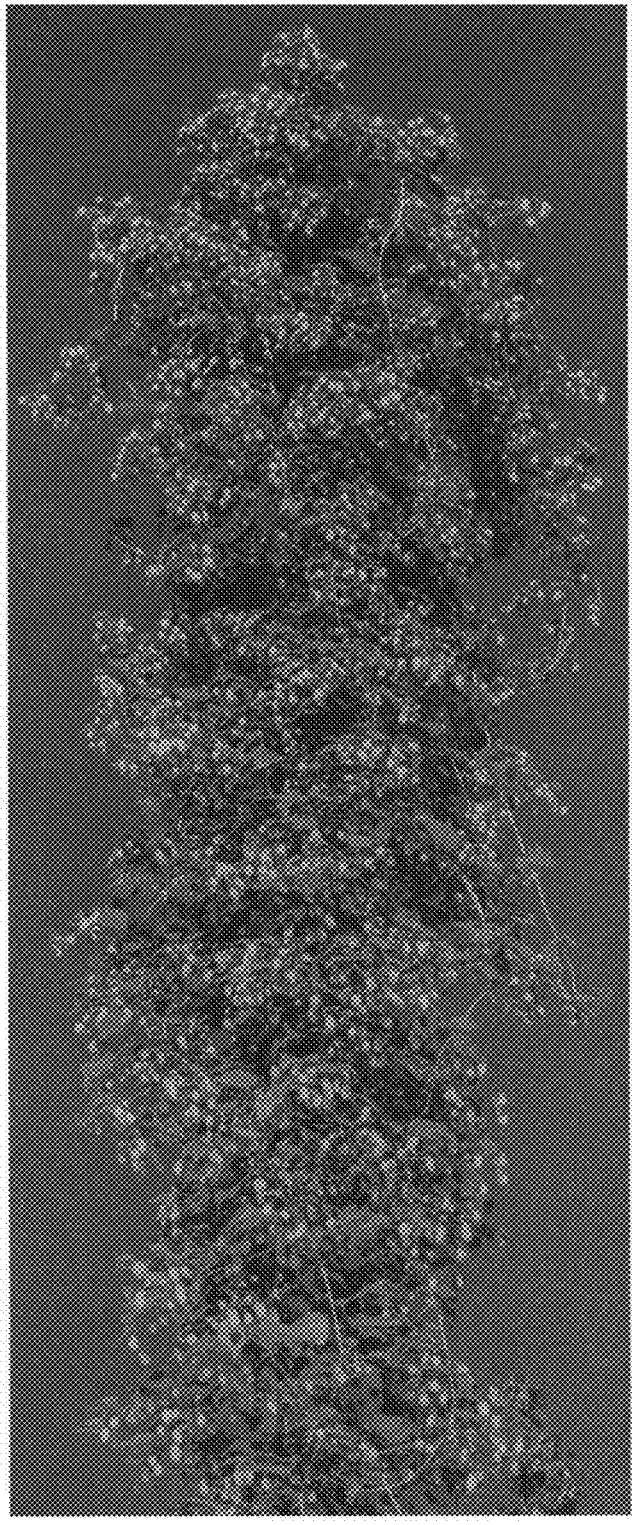
FIG. 3 illustrates the appearance of the plant and its cones as they are growing in the field on a high trellis of 7 meters (23.3 feet).

The following is a description of the new cultivar with colour terminology in accordance with The Royal Horticultural Society Colour Charts (R.H.S.C.C.) Sixth Edition (2015). The following description is based on observations made on adult (three years or more old) plants at the Žalec (Slovenia) location(s). It should be noted that characteristics described can vary with location, climate conditions, and agricultural practices. Measurements are presented as an average of measurements taken from a large number of individual plants of the new variety.

1. Parentage: A hop plant originating from a controlled cross pollination between a diploid Slovenian breeding line '272/138' female hop plant and Slovenian male hop plant 2/137, both unpatented.
2. Localities where grown and observed: Savinja Valley (Žalec and Gomilsko) and Carinthia region (Turiska vas).
3. Dates of first and last harvest: Approximately September 1 and September 15, respectively, in Savinja Valley; and, September 10 and September 20, respectively, in the Carinthia region.
4. Plant characteristics:
   - *Ploidy*.—Diploid.
   - *Plant*.—Green vigorous, climbing vine.
   - *Plant shape*.—Cylindrical to club-shaped.
   - *Plant*.—Volume of head: high.
   - *Side shoot from middle third of plant*.—Length: medium (e.g., between about 0.63 m and about 1 m).
   - *Side shoot from upper third of plant*.—Length: long (e.g., between about 0.8 m and about 1.15 m).
   - *Side shoot from middle third of plant*.—Density of foliage: sparse (e.g., between about 12 and about 17 leaves).
   - *Side shoot from middle third of plant*.—Number of cones per node: many (e.g., often times having about 13 cones per node on average).
   - *Side shoot from middle third of plant*.—Total number of cones: many (e.g., often times having about 58 cones per node on average).

*Side shoot from upper third of plant*.—Total number of cones: very many (e.g., often times having about 70 cones per node on average).

*Aroma*.—Passion fruit, mango, melon, lemon grass, and menthol.

*Bine color*.—Moderate yellow green (RHS 146C), no anthocyanin color.

*Bine stripe*.—Absent.

*Bine diameter* (*at 6 feet high*).—7.16 mm-9.8 mm at BBCH63, where the BBCH-scale is a scale that is used to identify the phenological development stages of a plant, and where BBCH63 refers to a flowering stage in which about 30% of a plant's flowers are open (see Growth Stages of Mono- and Dicotyledonous Plants, BBCH Monograph, 2. Edition, 2001, Federal Biological Research Centre for Agriculture and Forestry (Ed. Uwe Meier)).

*Bine length*.—23-27 feet.

*Petiole length*.—1.8-2.6 inches.

*Petiole color*.—183B (upper side).

*Leaf arrangement*.—Opposite.

*Mature leaf color*.—Upper surface dark green (RHS 137B).

*Mature leaf color*.—Lower surface green (RHS 137D).

*Mature leaf width*.—5.7-6.7 inches.

*Mature leaf length*.—4.7-6.0 inches.

*Number of main bine leaf lobes*.—5 (occasionally 3).

*Venation pattern*.—Palmately veined.

*Leaf margin*.—Biserrate (2).

*Leaf apex*.—Apical lobe or blade apex with marginal serrations.

*Leaf*.—Size of blade: small to medium (e.g., between about 14.2 cm and about 17.1 cm in width, and between about 11.9 cm and about 15.3 cm in length (without a petiole)).

*Leaf*.—Blistering of upper side of blade: weak-medium.

*Leaf*.—Intensity of green color of upper side of blade: medium; and.

*Time of flowering*.—Late (e.g., between July 1$^{st}$ and August 10$^{th}$).

5. Reproductive organs, cones, cone parts, seeds:

*Bract color* (*upper surface*).—Strong Yellowish Green (RHS N144A).

*Bract size*.—Medium (e.g., having a width between about 11 mm and about 13 mm and having a length between about 15 mm and about 17 mm).

*Bract ratio width/length*.—Large.

*Bract length of apex*.—Short (e.g., between about 1 mm and about 2 mm).

*Bract tip position*.—Mostly appressed like most hop varieties, as opposed to everted (turned out bracts) as seen in the variety of Galena.

*Bracteole shape*.—Lanceolate, similar to most hop varieties.

*Cone length*.—0.8 inch on average.

*Cone diameter*.—0.8-1.0 inch.

*Cone shape*.—Medium ovate.

*Cone weight*.—Average weight of 100 dry cones is 20 g.

*Cone*.—Degree of opening of bracts: closed.

*Cone*.—Intensity of green colour: medium.

*Yield per acre*.—1800-2200 pounds on average. However, this yield is dependent upon temperature, soil conditions; and cultural practices, and is therefore not distinctive of the present variety.

*Seeds*.—Highly variable in color and size depending on male parent; and.

*Date of maturity*.—Late (September 1st-September 10th) as compared to other common hop varieties grown in Slovenia.

6. Analytical data of cones:

% *Alpha-acids* (*bale*).—13.5-18.5% (Analytica-EBC, 7.7).

% *Beta-acids* (*bale*).—5.0-6.0% (Analytica-EBC, 7.7).

*Cohumulone* (% α-acids).—22-23.

*Colupulone* (% β-acids).—48-54.

*Xanthohumol* (% *w/w*).—0.6-0.8.

*Polyphenols* (% *w/w*).—4.7-5.7.

*Alpha/beta ratio*.—2.7-3.0.

*Storage characteristics*.—Very good (12% loss of alpha acids after 6 months at 22° C.).

*Total oils* (*mL*/100 *g hops*).—3.0-4.5.

*Myrcene* (*mL*/100 *g hops*).—60-70.

*Linalool* (*mL*/100 *g hops*).—0.8-1.3.

*Beta-caryophyllene* (*mL*/100 *g hops*).—2.0-3.0.

*Alpha-humulene* (*mL*/100 *g hops*).—5.0-9.0; and.

*Farnesene* (*mL*/100 *g hops*).—4.5-6.5.

7. Disease resistance and pest control: Field observations showed that the variety '74/134' is susceptible to primary (systemic) infection of hop downy mildew (*Pseudoperonospora humuli*) and resistant to downy mildew secondary infections. It has high resistance to powdery mildew fungus (*Podospheara macularis*) strains Vb, V3, and V5 which are currently present in Slovenia. No infections of Fusarium species, grey mold (*Botrytis cinerea*) and *Phytophthora citricola* were observed in monitored hop gardens. It is showing medium resistance to cercospora leaf spot disease (*Cercospora cantuariensis*), which could be dangerous in humid and warm conditions. Artificial inoculations of '74/134' by using verticillium wilt pathogens revealed medium resistance to *Verticillium nonalfalfae* (M-hop pathotype) and *V. dahliae* infections, and susceptibility to highly virulent strains (PV) of *Verticillium nonalfalfae*. Based on that it is not recommended for planting in regions where verticillium wilt is present. ELISA and RT-PCR tests of "nuclear stock" plants showed no infection of apple mosaic virus (ApMV), arabis mosaic virus (ArMV), hop mosaic virus (HpMV), hop latent virus (HpLV), hop latent viroid (HLVd), hop stunt viroid (HSVd), and citrus bark cracking viroid (CBCVd). Influence of hop viruses and viroids to '74/134' was not assessed yet. Field observations showed that two times spraying each with appropriate insecticide and acaricide have effectively controlled damson hop aphid (*Phorodon humuli*) and two spotted spider mite (*Tetranychus urticae*) infestations.

8. Ploidy: Hop variety '74/134' is diploid. The mother is diploid and the father is diploid as well.

9. Life expectancy: Similar to other hop varieties (e.g., while vegetative propagated species, such as hops, can maintain their genome essentially unchanged for years or even hundreds of years (because no sexual development is included), '74/134' (like other hop plants) can live for 15 years or more, noting that '74/134' plants that are older than 15 years (like other varieties of hop plants of that age) often times have a decreased quantity and quality yield).

10. Use: The variety '74/134' is known for its good agronomic traits in hop production and processing. It is distinguished by its very intense aroma, which has excellent transfer from hop cones into beer. Together with high alpha-acid content, it has very good brewing value for various kinds of beer. Flavoring and conditioning of beverages and foods and use as a vegetable. Used in breeding novel hop varieties.
11. Propagation status: '74/134' virus and viroid free propagation material exists. Asexual plant propagation has been demonstrated. In this regard, '74/134' is a vegetative propagated plant species in which asexual propagation allows for complete stability of the species to be achieved. '74/134' was asexually produced (through cuttings) for the first time in the Slovenian Institute of Hop Research and Brewing in Žalec, Slovenia to prepare plants for field trials. In some cases, '74/134' has been maintained in pots in a greenhouse and in in vitro conditions as well.
12. Reproductive status: '74/134' is fertile and produces seeds upon pollination with male hop plants.

The invention claimed is:

1. A new and distinct hop plant, named '74/134', as herein described and illustrated.

* * * * *